(12) United States Patent
Fearnot et al.

(10) Patent No.: US 9,579,080 B2
(45) Date of Patent: Feb. 28, 2017

(54) INTERNAL TRANSDUCER ASSEMBLY WITH SLIP RING

(71) Applicant: Muffin Incorporated, West Lafayette, IN (US)

(72) Inventors: Neal E. Fearnot, West Lafayette, IN (US); Peter S. McKinnis, West Lafayette, IN (US); Sarah Robbins, Lafayette, IN (US); Yun Zhou, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 26 days.

(21) Appl. No.: 14/051,844

(22) Filed: Oct. 11, 2013

(65) Prior Publication Data

US 2014/0107488 A1 Apr. 17, 2014

Related U.S. Application Data

(60) Provisional application No. 61/714,275, filed on Oct. 16, 2012.

(51) Int. Cl.
*A61B 8/12* (2006.01)
*A61B 8/00* (2006.01)
*A61B 17/29* (2006.01)
*H01R 39/08* (2006.01)
*A61B 17/00* (2006.01)
(Continued)

(52) U.S. Cl.
CPC ............... *A61B 8/12* (2013.01); *A61B 8/445* (2013.01); *A61B 8/4461* (2013.01); *A61B 8/4254* (2013.01); *A61B 8/56* (2013.01); *A61B 17/320758* (2013.01); *A61B 2017/00106* (2013.01); *A61B 2017/2929* (2013.01);
(Continued)

(58) Field of Classification Search
CPC .. A61B 17/320758; A61B 2017/00106; A61B 2017/2929; H01R 39/08; H01R 39/10; H01R 39/34; H01R 43/10; H02K 3/51
See application file for complete search history.

(56) References Cited

U.S. PATENT DOCUMENTS 2,790,095 A 4/1957 Peek et al.
4,421,118 A 12/1983 Dow et al.
(Continued)

FOREIGN PATENT DOCUMENTS

JP 06-209939 A 8/1994
JP 10-262974 A 10/1998
(Continued)

OTHER PUBLICATIONS

International Search Report and Written Opinion issued in PCT/US2013/064570, dated Jan. 24, 2014.
(Continued)

*Primary Examiner* — Long V Le
*Assistant Examiner* — Ellsworth Weatherby
(74) *Attorney, Agent, or Firm* — Woodard, Emhardt, Moriarty, McNett & Henry LLP (57) ABSTRACT

A device for internal ultrasound imaging including a micromotor rotates a drive shaft and ultrasound transducer. Conductors attach between the transducer and slip ring assemblies. The slip ring assemblies conductively couple the transducer conductors to a set of conductors extending toward a console.

18 Claims, 6 Drawing Sheets

(51) Int. Cl.
  *H02K 3/51* (2006.01)
  *H01R 39/34* (2006.01)
  *H01R 43/10* (2006.01)
  *A61B 17/3207* (2006.01)

(52) U.S. Cl.
  CPC .............. *H01R 39/08* (2013.01); *H01R 39/34* (2013.01); *H01R 43/10* (2013.01); *H02K 3/51* (2013.01)

(56) References Cited

U.S. PATENT DOCUMENTS

| | | | |
|---|---|---|---|
| 4,720,266 A * | 1/1988 | Leonard et al. | 433/126 |
| 4,785,816 A | 11/1988 | Dow et al. | |
| 4,811,617 A | 3/1989 | Whiteman, Jr. | |
| 4,951,677 A | 8/1990 | Crowley et al. | |
| 5,237,884 A | 8/1993 | Seto | |
| 5,373,845 A | 12/1994 | Gardineer et al. | |
| 5,437,283 A | 8/1995 | Ranalletta et al. | |
| 5,535,715 A | 7/1996 | Mouton | |
| 5,611,246 A | 3/1997 | Long et al. | |
| 5,729,508 A | 3/1998 | Baker et al. | |
| 6,241,744 B1 * | 6/2001 | Imran et al. | 606/159 |
| 6,248,074 B1 | 6/2001 | Ohno et al. | |
| 6,354,814 B1 | 3/2002 | Kaufmann et al. | |
| 6,371,915 B1 | 4/2002 | Koger et al. | |
| 6,684,094 B1 * | 1/2004 | Lehr et al. | 600/407 |
| 7,798,971 B2 | 9/2010 | Flesch et al. | |
| 8,206,307 B2 | 6/2012 | Barnard et al. | |
| 8,214,010 B2 | 7/2012 | Courtney et al. | |
| 2002/0082503 A1 | 6/2002 | Chandrasekaran et al. | |
| 2002/0087083 A1 | 7/2002 | Nix et al. | |
| 2002/0143252 A1 | 10/2002 | Dunne et al. | |
| 2005/0203416 A1 | 9/2005 | Angelsen et al. | |
| 2006/0030797 A1 | 2/2006 | Zhou et al. | |
| 2006/0173348 A1 | 8/2006 | Wilser et al. | |
| 2007/0038110 A1 | 2/2007 | Flesch et al. | |
| 2007/0038114 A1 | 2/2007 | Couvillon, Jr. | |
| 2007/0149917 A1 | 6/2007 | Bennett et al. | |
| 2007/0167813 A1 | 7/2007 | Lee et al. | |
| 2007/0167821 A1 | 7/2007 | Lee et al. | |
| 2008/0097403 A1 | 4/2008 | Donaldson et al. | |
| 2008/0177138 A1 | 7/2008 | Courtney et al. | |
| 2008/0221506 A1 | 9/2008 | Rodriguez et al. | |
| 2008/0234716 A1 | 9/2008 | Kiester | |
| 2008/0243035 A1 | 10/2008 | Crunkilton | |
| 2008/0319376 A1 | 12/2008 | Wilcox et al. | |
| 2009/0051121 A1 | 2/2009 | Sokek et al. | |
| 2009/0088631 A1 | 4/2009 | Dietz et al. | |
| 2009/0306518 A1 | 12/2009 | Kurse et al. | |
| 2010/0036258 A1 | 2/2010 | Dietz et al. | |
| 2010/0145310 A1 | 6/2010 | Lee et al. | |
| 2010/0160788 A1 | 6/2010 | Davies et al. | |
| 2010/0179426 A1 | 7/2010 | Davies et al. | |
| 2010/0217125 A1 | 8/2010 | Kadokura et al. | |
| 2010/0234736 A1 | 9/2010 | Corl | |
| 2010/0249601 A1 | 9/2010 | Courtney | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0071400 A1 | 3/2011 | Hastings et al. | |
| 2011/0071401 A1 | 3/2011 | Hastings et al. | |
| 2011/0196286 A1 * | 8/2011 | Robertson et al. | 604/22 |
| 2011/0237955 A1 | 9/2011 | Dietz et al. | |
| 2011/0263986 A1 | 10/2011 | Park et al. | |
| 2011/0301508 A1 | 12/2011 | Sethuraman et al. | |
| 2012/0108980 A1 | 5/2012 | Shilling et al. | |
| 2012/0172698 A1 | 7/2012 | Teo et al. | |
| 2013/0066304 A1 | 3/2013 | Belson et al. | |

FOREIGN PATENT DOCUMENTS

| | | |
|---|---|---|
| JP | 2000-126184 A | 5/2000 |
| JP | 2001-046375 A | 2/2001 |
| JP | 2004/129697 | 4/2004 |
| JP | 2007-267998 A | 10/2007 |
| WO | WO 2012/061643 A1 | 5/2012 |

OTHER PUBLICATIONS

International Search Report and Written Opinion issued in PCT/US2013/064579, dated Jan. 23, 2014.
International Search Report and Written Opinion issued in PCT/US2013/064606, mailed Jan. 8, 2014.
International Search Report and Written Opinion issued in PCT/US2013/064611, dated Jan. 28, 2014.
International Search Report and Written Opinion issued in PCT/US2013/064618, dated Jan. 24, 2014.
International Search Report and Written Opinion issued in PCT/US2013/078245, dated Apr. 25, 2014.
International Search Report and Written Opinion issued in PCT/US2014/023088, dated Aug. 18, 2014, 14 pgs.
International Search Report and Written Opinion issued in PCT/US2014/023092, dated Aug. 12, 2014, 16 pgs.

\* cited by examiner

INTERNAL TRANSDUCER ASSEMBLY WITH SLIP RING

CROSS-REFERENCE TO RELATED APPLICATION

This application claims the benefit of U.S. Provisional Application No. 61/714,275 filed Oct. 16, 2012, which is hereby incorporated by reference.

This disclosure concerns devices and methods for using ultrasound within the body of a patient. In particular, it concerns features that allow such devices to be reduced in size for use in small body areas, such as within blood vessels.

BACKGROUND

Ultrasound technology has been used for therapeutic and diagnostic medical procedures, which can include providing imaging of internal portions of a body. Ultrasound procedures typically use a transducer assembly to emit and/or receive signals. In some cases, a stationary transducer assembly can view a full image area due to the particular positioning or electronic steering of the multiple ultrasound elements in an array. Another design includes a rotating transducer assembly having a single ultrasound element which obtains data by mechanically rotating the transducer assembly. In that case, data is obtained by the transducer assembly emitting sequential ultrasound pulses at changing rotational positions. Advantages of the single-element rotational design when compared to an array design include smaller catheter diameter, better image quality, possible higher center frequency, lower cost for the ultrasound imaging console, and less ring down artifacts (dead zone).

Single element designs can also include certain disadvantages, such as non-uniform rotational distortion (NURD). During imaging procedures including a single element design, the ultrasound element is typically rotated with a torque cable. Ultrasound pulses are emitted in an even-spaced time-sequential manner under the expectation of a uniform rotation rate of the ultrasound element. Each reflected ultrasound echo signal represents a portion or scan line of an image. An image processor assembles the data based on the assumption that the data points represent images from evenly-spaced pulses. However, it can be difficult to achieve a uniform rotation rate for the ultrasound element when using a torque cable as a driving means. The ultrasound element can be around one meter from the driving end of the torque cable. Ideally, the torque cable will have sufficient stiffness to provide uniform rotation at both ends while simultaneously allowing maneuverability. However, practically a sufficiently maneuverable torque cable creates a potential for delay in the transferring of torque from one end of the cable to the other, as the cable stores and releases elastic energy, which causes the transducer assembly to rotate at a non-uniform rate even when the rotation source rotates at a uniform rate. The non-uniform rotation rate causes the resulting images to be distorted.

Attempts to create single element designs without torque cables present further problems. Designs which include a microminiature motor positioned near a stationary transducer assembly and a rotating reflector require additional space. In addition, control wires or structural components can cross the viewing window causing a portion of an image to be blocked. Another problem is the possibility of breaking a catheter tip which includes the ultrasound transducer. Designs including a microminiature motor positioned near a rotating transducer assembly present further problems. Current commercialized designs use costly and bulky rotary transformers to connect stationary electrical wires from a console to a rotating ultrasound element. However, the rotary transformer is among the most expensive components of such imaging systems.

Other problems exist in current designs. Typically, transducer assemblies are positioned in a dedicated catheter. The catheter usually shares the same utility lumen as therapeutic catheters preventing a physician from performing imaging monitoring simultaneously with or during additional procedures, such as, for example, deploying a stent or graft or performing a biopsy.

Thus, there is a need to have an ultrasound system design that could be integrated with a catheter, that is cost effective, small in size, and which produces images free from NURD artifacts and blocked viewing areas.

SUMMARY

Among other things, there are disclosed embodiments of devices for medical ultrasound application within a patient, and methods for making and using them. For example, a device for medical ultrasound in particular embodiments includes a motor operatively coupled with a drive shaft extending substantially along a rotation axis, wherein operation of the motor rotates the drive shaft around the rotation axis, and a transducer configured for transmitting and/or receiving ultrasound signals and operatively coupled with the drive shaft so that the transducer rotates in response to rotation of the drive shaft. A first slip ring assembly having a first rotational contact and a first stationary contact is provided, with the first rotational contact being fixed to the drive shaft and rotatable with the drive shaft relative to and in contact with the first stationary contact, so that the first slip ring assembly maintains an electrical conduction path between the first rotational contact and the first stationary contact while the drive shaft is rotating. A second slip ring assembly having a second rotational contact and a second stationary contact is provided, with the second rotational contact being fixed to the drive shaft and rotatable with the drive shaft relative to and in contact with the second stationary contact, so that the second slip ring assembly maintains an electrical conduction path between the second rotational contact and the second stationary contact while the drive shaft is rotating.

Particular embodiments in which the first and second rotational contacts are electrically conductive layers fixed with respect to the drive shaft are also described. For instance, the first rotational contact can be radially inward of the second rotational contact, with the first and second rotational contacts being separated by an insulating layer. The first rotational contact and the insulating layer have respective lengths measured parallel to a rotation axis of the drive shaft, and examples in which the length of the first rotational contact is larger than the length of the insulating layer are contemplated. Two axially outer portions of the first rotational contact can be exposed from the insulating layer. The length of the insulating layer can be larger than the second rotational contact's length measured parallel to a rotation axis of the drive shaft, e.g. so that two axially outward portions of the insulating layer are exposed from the first rotational contact. Such exposed portions can be used as contact areas for engagement between one or both of the rotational contacts and the respective stationary contact(s). Thus, the first rotational contact and first stationary contact may be in contact with each other at a point on an application side of the insulating layer, and/or the second rotational contact and second stationary contact may be in contact with each other at a point on a control side of the insulating layer. An insulating section is disposed in some embodiments between the first stationary contact and the second stationary contact, and may be disposed to contact the insulating layer. One specific example of such contacts and layers provides the first and second rotational contacts as part of a three-layer coating, the first rotational contact being a radially inward first layer, an insulating layer being a second layer, and the second rotational contact being a radially outward third layer. The insulating layer partially covers the first rotational contact and the second rotational contact partially covers the insulating layer.

Illustrated embodiments include a fluidly sealed chamber enclosing the transducer and having an interior in fluid communication with the first stationary contact and the transducer. When an electrically conductive fluid is disposed within the chamber, the electrically conductive fluid creates a conduction path between the transducer and either the first rotational contact or the second rotational contact.

Other embodiments include a device for medical ultrasound which includes a transducer configured for transmitting and/or receiving ultrasound signals and operatively coupled with a drive shaft extending substantially along a rotation axis. The transducer rotates in response to rotation of the drive shaft. A motor is operatively coupled with the drive shaft, and includes a first slip ring assembly having a first rotational contact and a first stationary contact. The first rotational contact is fixed relative to the drive shaft and rotatable with the drive shaft relative to and in contact with the first stationary contact. The first slip ring assembly maintains an electrical conduction path between the first rotational contact and the first stationary contact when the drive shaft rotates.

Particular embodiments include the motor being a piezoelectric motor including a stator and a first clutch coupled with the shaft and disposed to engage a piezoelectric element, wherein the first clutch includes the first rotational contact. The stator can include the first stationary contact. The motor can include a second slip ring assembly having a second rotational contact and a second stationary contact. The second rotational contact can be fixed relative to the drive shaft and rotatable with the drive shaft relative to and in contact with the second stationary contact. The second slip ring assembly can maintain an electrical conduction path between the second rotational contact and the second stationary contact when the drive shaft rotates. The first rotational contact is electrically insulated from the second rotational contact and the first stationary contact is electrically insulated from the second stationary contact. The stator can include a first end and a second end, wherein the second end is positioned opposite the first end in an axial direction relative to the rotation axis. The first clutch can be disposed adjacent to the first end and the second clutch can be disposed adjacent to the second end. A first insulating layer can be positioned between the first stationary contact and the first end, and a second insulating layer can be positioned between the second stationary contact and the second end.

Other particular embodiments can include a second slip ring assembly having a second rotational contact and a second stationary contact, the second rotational contact being fixed relative to the drive shaft and rotatable with the drive shaft relative to and in contact with the second stationary contact. The second slip ring assembly can maintain an electrical conduction path between the second rotational contact and the second stationary contact when the drive shaft rotates. The first rotational contact can be electrically insulated from the second rotational contact. A first end of the first rotational contact can be disposed to contact the first stationary contact and a second end of the second rotational contact can be disposed to contact the second stationary contact, wherein during rotation of the drive shaft, the first end follows a first circumferential path about the rotation axis and the second end follows a second circumferential path about the rotation axis. The first circumferential path can be positioned concentric to and radially inward of the second circumferential path, and the first stationary contact can be positioned radially inward of the second stationary contact. In other embodiments, a first end of the first stationary contact is disposed to contact the first rotational contact and a second end of the second stationary contact is disposed to contact the second rotational contact. The second end is positioned radially outward from the first end relative to the rotation axis, and the second rotational contact is positioned concentric to and radially outward of the first rotational contact. A disk can be coupled with the shaft and anchoring the first and second rotational contacts. The first and second stationary contacts can be positioned in a plane which is normal to the rotation axis.

A biasing member can be disposed to apply a force which maintains contact between the first rotational contact and the first stationary contact. At least one of the contacts can be coated with a precious metal. An encapsulating structure fillable with a fluid can be positioned to enclose the slip rings whereby the fluid reduces friction and/or prevents oxidation.

DESCRIPTION OF THE ILLUSTRATED EMBODIMENTS

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates.

Referring generally to the drawings, there are shown embodiments of a device 20 suitable for endoluminal medical procedures. Device 20 can be used with a system that includes a console (not shown) and device 20. In some cases the system can be an imaging system. The ultrasound console can be a type which is generally used for medical ultrasonic imaging, e.g. generally including control devices usable by a physician and a graphic display which displays graphical images obtained during an ultrasound procedure. Device 20 can be used for obtaining images at various locations of a body such as a blood vessel, urethra, ureter, vagina, rectum, throat, ear, or through an artificial tract (or lumen) by percutaneous puncture for example. The console portion can be connected to commercially available ultrasound probes or catheters with compatible pinout, or other medical devices which are configured for endoluminal procedures. Device 20 is capable of emitting and receiving ultrasound signals and then communicating data obtained from ultrasound signals to the console. The console is configured to process the data and create image(s) viewable on a display or other data output.

Figure 1:
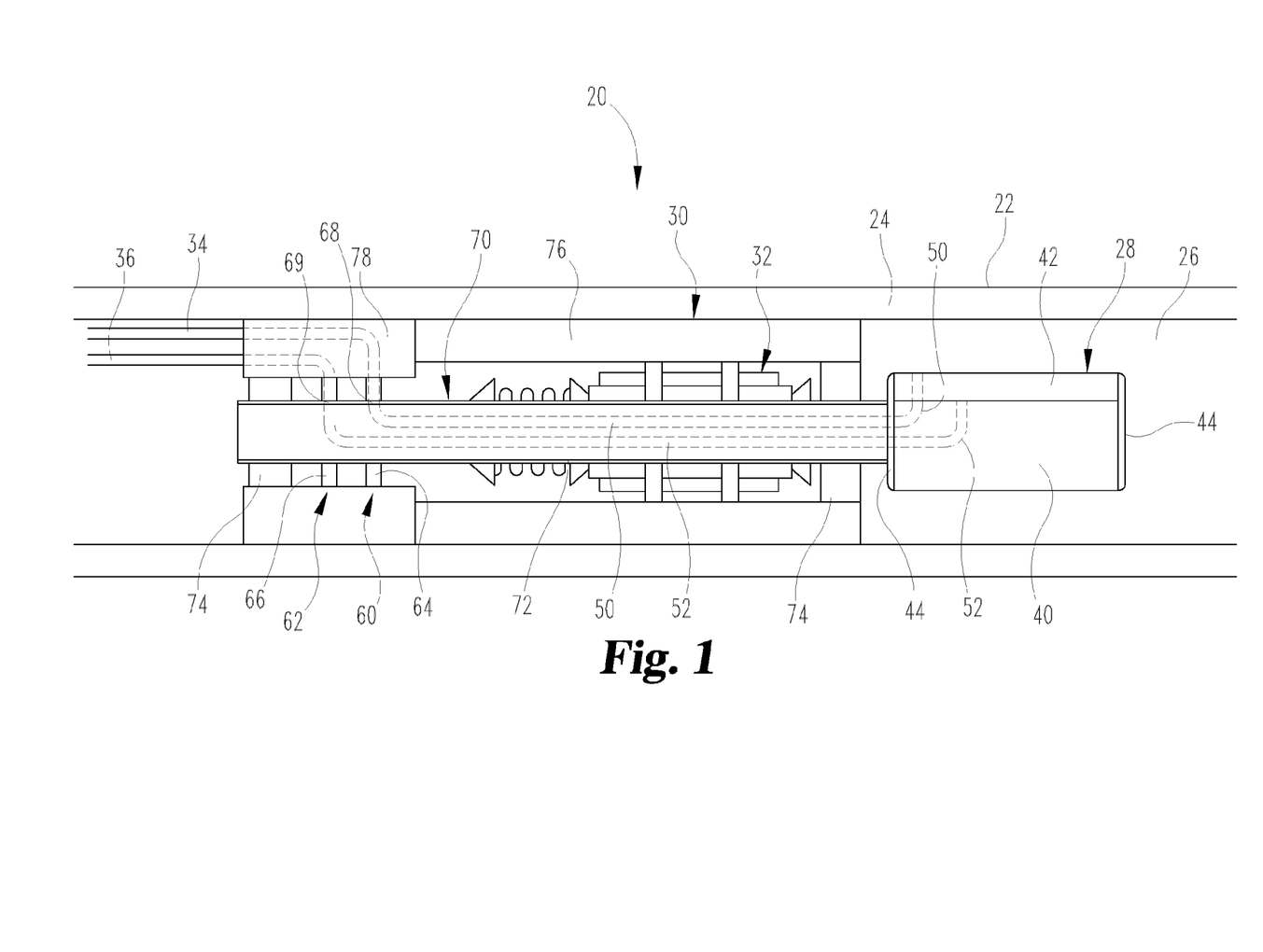
FIG. 1 is a cross-sectional view of an ultrasound imaging device with a slip ring assembly positioned on a control side of a motor.

In the embodiment shown schematically in FIG. 1, device 20 includes a catheter 22 or other flexible elongated member having a wall 24 defining an internal chamber 26. Catheter 22 is sized and configured for insertion into and/or travel along bodily orifices or lumens. Positioned within chamber 26 is a transducer 28 and a motor 32 operatively coupled with transducer 28. Generally, catheter 22 provides access to a bodily location where motor 32 provides rotational motion to transducer 28. Device 20 could optionally include a motor housing (not shown) for providing structural support for motor 32 and transducer 28. Transducer 28 in conjunction with rotary motion provided by motor 32 is capable of transmitting and receiving ultrasound signals in a variety of directions which are passed along data signal communication lines (i.e. conductors, or conduction pathways) between transducer 28 and the ultrasound console.

Catheter 22 in the illustrated embodiment is an elongated device of plastic or other sturdy flexible material which presents a barrier to the passage of ultrasound signals which is small enough that ultrasound images may be reasonably acquired through the barrier. Catheter 22 includes a control end which during use is nearest to the user and an application end which during use is nearest to the user's point of interest. The terms "control" and "application" are used throughout this description to describe these positional orientations. Wall 24 surrounds chamber 26, which is at the application end of device 20 in the illustrated embodiment. The control end of wall 24 and/or catheter 22 may extend outside of the patient during use, (or may attach to another component that extends outside the patient), and may end in a handle or other operating portion for maneuvering catheter 22. Particular embodiments of catheter 22 or at least chamber 26 are cylindrical, and are sized for insertion into and passage through bodily orifices and lumens, such as insertion into the femoral artery and passage through it toward the heart. Wall 24 may have a port or other feature to allow injection of fluid into chamber 26, as will be discussed further below.

Catheter 22 is constructed of a material which is substantially echolucent when placed in the surrounding working environment (such as blood within a blood vessel) such that it acts as an acoustic window which allows passage of ultrasound signals with minimal attenuation. Echolucency is a result of an ultrasound wave conduction path having mediums with substantially matched acoustic impedances. For example, when used within a blood vessel containing body tissues and blood, it is preferable for catheter 22 to be constructed of a material which is structurally rigid and which has acoustic impedance similar to that of body fluids such as blood. Possible materials could include, for example, a polymer material such as high density polyethylene, polymethylpentene (PMP), or acrylonitrile butadiene styrene (ABS). It has been determined that in some cases the thickness of at least the portion of catheter 22 which serves as the viewing window can be approximately N/2 (where N is a positive integer) of the wavelength corresponding to center frequency.

Transducer 28 is indicated schematically in the drawings. The term "transducer" should be understood to include an assembly of two or more parts as well as a single piece. An exemplary transducer 28 includes a body or backing 40 with an ultrasound element 42 attached to one side of backing 40, and one or more clamping rings 44. Transducer 28 can include a matching layer (not shown) attached to one side of element 42. Element 42 can be a piezoelectric element which has the ability to convert electrical energy into sound waves and sound waves into electrical energy. The positioning of element 42 as indicated, on a side of backing 40, results in a directed ultrasound beam direction. Backing 40 may be substantially opaque to ultrasound signals, so that such signals are effectively only projected outward from element 42, e.g. to one side or in a limited angular range radially (relative to a rotation axis) from backing 40. The matching layer has acoustic impedance generally between that of element 42 and the medium surrounding transducer 28 in order to minimize mismatched acoustic impedance between transducer 28 and the medium surrounding transducer 28. Transducer 28, as discussed, can be a single element transducer which is capable of sending and receiving ultrasound waves in a range of frequencies which are typically used in medical ultrasound procedures, such as, for example, in the range from 20 KHz to 100 MHz. Clamping rings 44 have been determined to improve efficiency and add mechanical stability to transducer 28.

Motor 32 is a microminiature motor of a small size which is suitable for containment within chamber 26 of catheter 22. Microminiature motors such as small piezoelectric motors, electromagnetic motors, or shape memory motors may be used. In one embodiment, the motor is a three-phase, coreless, brushless DC electromagnetic motor, which has few components, small size and minimal complexity. Another embodiment includes a piezoelectric motor. A piezoelectric motor is preferably of a small size, such as having a diameter in the range from 0.3 mm to 4 mm. An advantage of a piezoelectric motor compared to other motors such as electromagnetic motors is that the efficiency of the piezoelectric motor is independent of size such that microminiature piezoelectric motors can exhibit a high torque-to-size ratio relative to other motors. The use of such microminiature motors can eliminate problems with torque cables Motor 32 includes a rotating shaft 70, for direct or indirect connection to transducer 28. It has been determined that hall sensors are advantageous as a feedback mechanism because of their small size and mature design. In some embodiments, the ultrasound beam or signals emitted and/or received by transducer 28 is used as a feedback mechanism to precisely assess or monitor the rotational position of motor 32 (and the ultrasound beam rotated by it) relative to the rest of device 20, ensuring proper registration of images obtained through transducer 28. A seal 74, bearing, or other structure is positioned adjacent to motor 32 and shaft 70 to provide a fluid seal between the motor and the chamber surrounding transducer 28.

Shaft 70 can be a hollow cylindrical shaft in the illustrated embodiments, having a lumen 72 extending therethrough. Shaft 70 extends through the entirety of motor 32. Lumen 72 permits passage of electrical conductors, (e.g. wires, cables, guide wires), mechanical operational items (e.g. guide wires), and/or other features to pass through shaft 70, allowing transmission of electrical and/or mechanical force or energy through lumen 72 without affecting the rotation of shaft 70. Transducer 28 is operatively connected to shaft 70 so that transducer 28 rotates in response to rotation of shaft 70.

Transducer 28 is operatively coupled with shaft 70 in this embodiment so that its longitudinal axis is parallel to or coincident with the rotation axis of shaft 70. Element 42 is positioned in this embodiment so that an ultrasound beam or signals emitted from element 42 travel outward from the rotation axis. Similarly, element 42 receives an ultrasound beam or signals from directions outward of the rotation axis. Transducer 28 can be coupled directly to shaft 70. Alternatively, transducer 28 in one example could be coupled with shaft 70 through use of an intermediate support (not shown). The intermediate support can be hollow and defining an inner lumen in a similar manner as shaft 70.

A portion of chamber 26 immediately surrounding transducer 28 extending towards the application end of catheter 22 can be completely filled with a fluid or other substance having acoustic impedance similar to that of blood, such as saline, oils (e.g. mineral oil or castor oil), or mixed alcohol. The substance should minimize friction acting against transducer 28 during rotation. In this way, acoustic matching can be achieved between body fluids, catheter 22, and the medium immediately surrounding transducer 28. Acoustic matching ensures that minimal signal losses occur when transmitting and receiving ultrasound signals between transducer 28 and body tissue which enhances the clarity of the resulting image.

The fluid can be added to device 20 during manufacture, or alternatively could be added prior to use. When the transducer is sealed and the coupling fluid is placed into the chamber during manufacture, long term contact with the parts necessitates a non-corrosive fluid such as mineral oil or castor oil in order to preserve the shelf life of the product. Preferably, the oil is bio-compatible, acoustically transparent, and has low viscosity. Alternatively, a fluid communication port positioned within the catheter or through the catheter wall can allow access for adding a fluid, in which case a corrosive fluid may be used. Corrosive fluids such as water, saline, and alcohol typically have more favorable combinations of bio-compatibility, acoustic transparency and viscosity.

In the embodiment of FIG. 1, electronic signals pass between an ultrasound console and transducer 28 via fixed conductors (e.g. wires) 34, 36, and rotating conductors 50, 52 connected to transducer 28 and extending through lumen 72 in rotatable shaft 70. A pair of slip ring assemblies 60, 62 facilitate transfer of such signals between rotating conductors 50, 52 and non-rotating conductors 34, 36. In the FIG. 1 embodiment, two slip ring assemblies 60, 62 each having a single conduction path are shown. However, a design could include a single slip ring assembly that includes one or two conduction paths. In the FIG. 1 embodiment, a two channel electrical connection includes conductor 50 as a signal channel and conductor 52 as a ground channel. Conductors 50, 52 can be attached at a variety of locations to element 42, depending on the requirements of the particular configuration. Conductors 50, 52 can be thin wires which extend through backing 40 and/or clamping rings 44 and into lumen 72. Alternatively, conductors 50, 52 can extend from the sides of transducer 28 and sealingly enter lumen 72 through a sealed port (not shown). Alternatively, backing 40 can be conductive so that the whole backing is part of the conduction path between the element 42 and one or both conductors 50, 52. Similarly, the matching layer could be a conductive layer which is part of the conduction path between element 42 and one or both conductors 50, 52.

Slip ring assemblies 60, 62 include stationary contacts 64, 66 and rotational contacts 68, 69. In the FIG. 1 embodiment, stationary contacts 64, 66 are conductive filaments and rotational contacts 68, 69 are conductive rings positioned around the circumference of shaft 70. However, in other embodiments rotational contacts 68, 69 could be filaments and stationary contacts 64, 66 could be conductive rings. The conductive rings include a conductive circle or band fixed to shaft 70 and insulated from each other (and from shaft 70 in embodiments in which shaft 70 is electrically conductive). The conductive rings are disposed to maintain contact with the filaments even when shaft 70 rotates, transferring electric signals between the rotating portion and the stationary portion. Slip ring assemblies using components other than filaments are also contemplated, such as the use of fixed (e.g. spring) contacts or brushes for example.

Slip ring assemblies 60, 62 maintain a conduction pathway between stationary contacts 64, 66 (connected to fixed conductors 34, 36) and rotational contacts 68, 69 (connected to rotating conductors 50, 52) during rotation through use of the sliding contact between the stationary contacts and the conductive surface of the rotational contacts. A portion of rotational contacts 68, 69 can pass through the wall of shaft 70 to couple with conductors 50, 52. Alternatively, conductors 50, 52 can pass through the wall of shaft 70 to couple with rotational contacts 68, 69. Conductors 50, 52 can be attached to rotational contacts 68, 69 through soldering or other techniques. Ends of conductors 34, 36 are conductively attached to stationary contacts 64, 66 using similar techniques. The conductors 34, 36 pass through a lateral wall 78 and extend throughout the catheter 22 to eventually conductively connect with the ultrasound console. In the embodiment of FIG. 1, slip ring assemblies 60, 62 are each positioned on the control side of motor 32, i.e. their respective contacts are on or adjacent to a portion of shaft 70 extending from the control side from motor 70.

During operation of the device 20, a physician moves device 20 into the body (e.g. the circulatory system) and positions device 20 and catheter 22 within the body of a patient at a desired location. Once device 20 is properly positioned, motor 32 is powered such that shaft 70 rotates, e.g. at a uniform angular velocity. Correspondingly, transducer 28 rotates about the rotation axis. Element 42 is energized through conductors 50, 52 which receives power from the ultrasound console. Element 42 transmits an ultrasound signal substantially in an outward direction relative to shaft 70 in this embodiment, i.e. substantially perpendicular to the rotation axis.

When an ultrasound signal is transmitted, the ultrasound signal passes across wall 24 of catheter 22 until it encounters an acoustic impedance boundary (e.g. body tissue, plaque, or other material which has acoustic impedance sufficiently different from bodily fluids or other surrounding material) such that the ultrasound signal is partially reflected at the surface of the body tissue. A portion of the ultrasound signal is reflected back towards transducer 28. Simultaneously or subsequently transducer 28 continues to transmit further ultrasound signals and the process is repeated, continuously in certain embodiments over a desired period of time.

Transducer 28 is rotated about the rotation axis such that the ultrasound beam moves in a sweeping direction which takes the form of a slice, cone, or toroidal shape. In this manner, while transducer 28 rotates about the rotation axis, element 42 is able to emit and receive ultrasound signals sufficient for the ultrasound imaging system to create a 2D image representative of bodily tissue adjacent to or near catheter 22. According to the specifics of the ultrasound imaging procedure or the desires of the physician performing the procedure, the device 20 can be moved in an axial direction within a bodily orifice such that multiple two-dimensional images are created at different locations within the bodily orifice. In this way, the two dimensional images can be processed into a three dimensional image or alternatively the physician can gain a three dimensional conceptual understanding of the physical features of bodily tissue adjacent to catheter 22.

Figure 2:
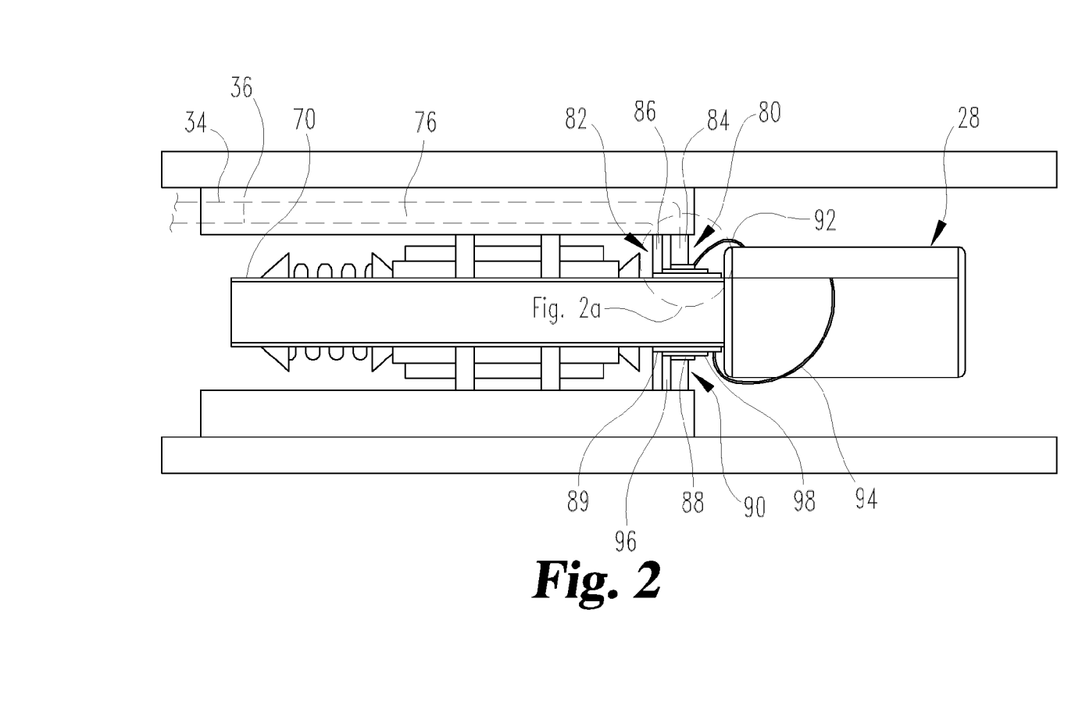
FIG. 2 is a cross-sectional view of an ultrasound imaging device with a slip ring assembly positioned on an application side of the motor.
Figure 2A:
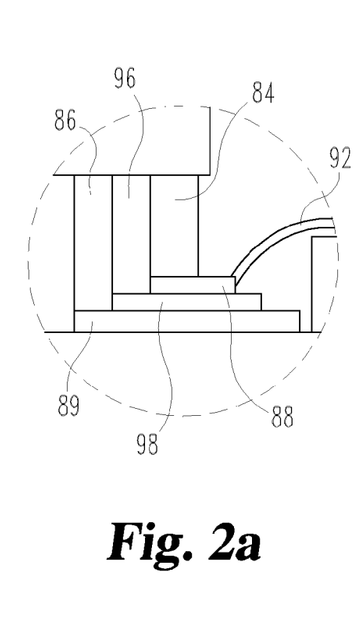
FIG. 2a is an enlarged view of a portion of the slip ring assembly of FIG. 2.

An alternative embodiment of device 20 is shown schematically in FIG. 2. Device 20 includes a bearing 90 which has integrated slip ring assemblies 80, 82. Bearing 90 in FIG. 2 is not drawn to scale and is included merely for illustrative purposes in order to visually depict the embodiment described herein. Bearing 90 has stationary contacts 84, 86 and rotational contacts 88, 89. Stationary contacts 84, 86 may be brushes, as noted above, or may be formed by applying a conductive coating to a non-conductive bearing surface such as a polymer or ceramic. It has been determined that cobalt-doped gold (e.g. hard gold) is a good candidate for a conductive plating material because of its low resistance electrical connection and favorable mechanical wearing properties. Other plating materials could also be used, such as precious metals, platmium or rhodium for example. A nonconductive section 96 (or stationary insulating section) of bearing 90 is maintained between stationary contact 84 and stationary contact 86 as an insulative section.

Rotational contacts 88, 89 are fixed to shaft 70 and so rotate along with shaft 70. In this embodiment, each contact 88, 89 is a layer of conductive material, and they are separated by a central layer 98 of insulating material. Each layer may be applied separately, or as another example can be formed from a three-layer coating which is added to the surface of shaft 70. Rotational contact 89 is a base layer on the surface of shaft 70, or if shaft 70 is conductive, is over an insulating layer (not shown) on the surface of shaft 70. Insulating layer 98 (i.e. a second or central layer) is applied at least partially over rotational contact 89. The outer edge portions of the conductive layer of rotational contact 89 are exposed with respect to layer 98 in this embodiment (i.e., portions extending in an axial direction relative to the rotation axis and further than the edges of layer 98), so that contact 89 can conductively interact with stationary contact 86. Rotational contact 88 is applied on central layer 98, with two outer edge portions of central layer 98 exposed from contact 88 in this embodiment so as to maintain insulation between rotational contact 88 and rotational contact 89. Rotational contacts 88, 89 align with and contact stationary contacts 84, 86, respectively. Thus, this embodiment of contacts 88, 89 and layer 98 essentially form a sandwich with insulating central layer 98 between contacts 88, 89, and with exposed outer (or outward) portions of contacts 88, 89 contacting stationary contacts 84, 86.

Conductors 92, 94 conductively couple transducer 28 to rotational contacts 88, 89. Rotational contacts 88, 89 conductively couple with stationary contacts 84, 86. Stationary contacts 84, 86 are connected to fixed conductors (e.g. wires or cable(s)) which extend through lateral wall 76 and which are electrically operatively coupled with the ultrasound console.

Figure 3:
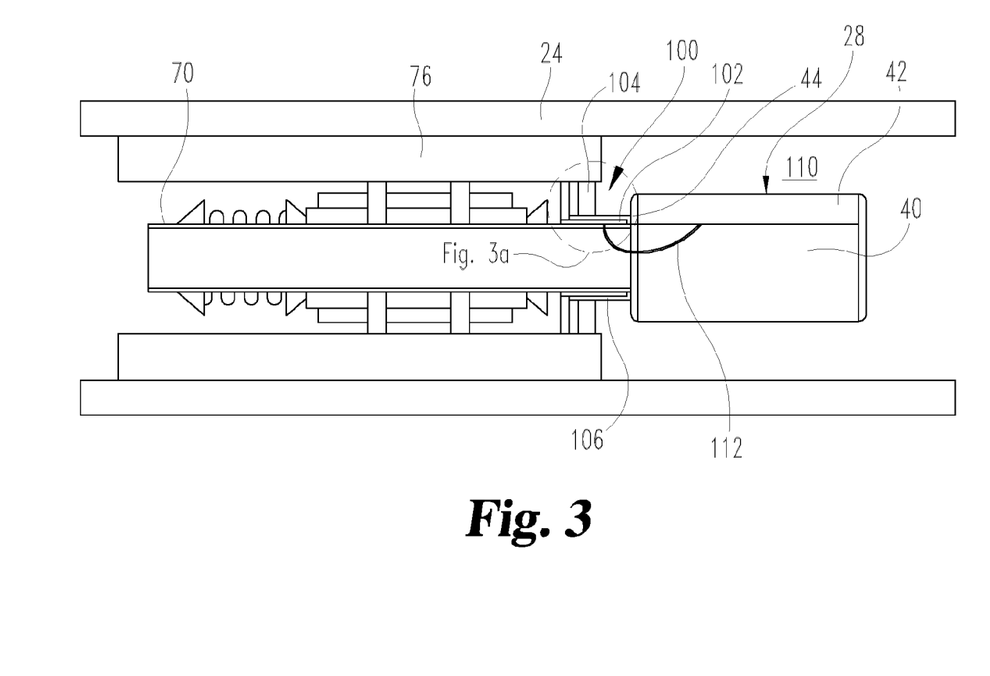
FIG. 3 is a cross-sectional view of an ultrasound imaging device with a slip ring assembly positioned on an application side of the motor, and a fluid acting as a conductor.
Figure 3A:
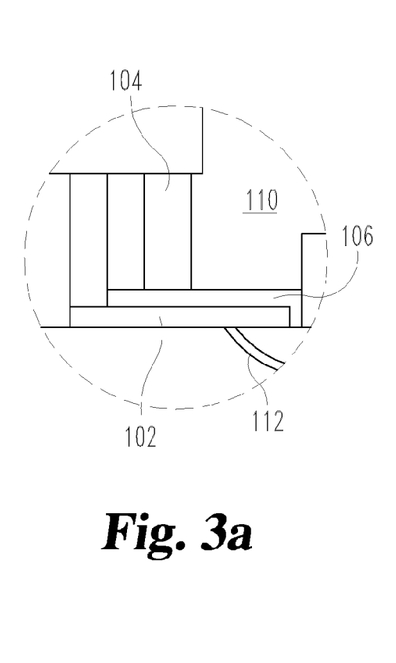
FIG. 3a is an enlarged view of a portion of the slip ring assembly of FIG. 3.

A further alternative embodiment of device 20 is shown schematically in FIG. 3. In this embodiment, device 20 includes a fluid conductor 110 and a wired conductor 112. Device 20 includes bearing 100 which is similar to the embodiment of FIG. 2, however it does not include a third layer as part of the rotational contact. Additionally, the central insulative layer 106 positioned on shaft 70 extends in the application side direction to sealingly isolate rotational contact 102 from any fluid positioned adjacent to bearing 100. Conductor 112 can pass through backing 40, and/or clamping ring 44, and a wall of shaft 70 in order to conductively couple with rotational contact 102. Conductor 110 provides an electric conduction path between element 42 and stationary contact 104. Alternatively, the matching layer could be a conductor which is part of a conduction path between element 42 and conductor 110. Conductor 110 can be any of a variety of electrically conductive fluids. Testing has shown that 10× concentrated phosphate buffered saline is one suitable conductive fluid. Conductor 110 has acoustic properties similar to wall 24 and body fluids in order to provide matching acoustic characteristics between conductor 110, wall 24, and body fluids, as well as lubricious qualities and other characteristics as described in relation to the embodiment of FIG. 1. The FIGS. 2 and 3 embodiments provide the advantage that device 20 can be smaller and more compact by positioning slip rings between transducer 28 and motor 32.

Figure 4:
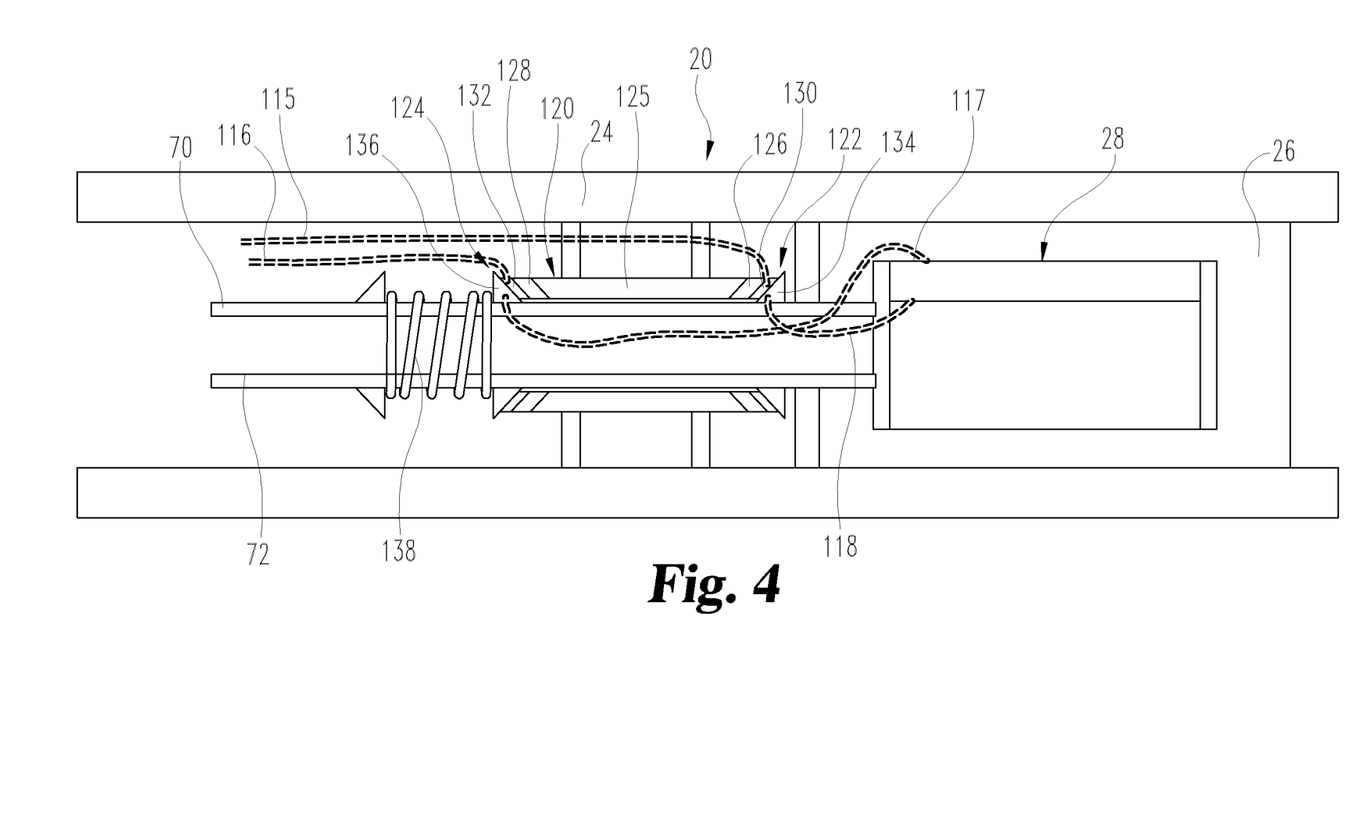
FIG. 4 is a cross-sectional view of an ultrasound imaging device with a slip ring assembly included in a motor.

A further alternative embodiment of device 20 is shown in FIG. 4. In this embodiment, electric signals are passed between the ultrasound console and transducer 28 via fixed conductors 115, 116 and rotating conductors 117, 118 connected to transducer 28 and extending through lumen 72 in rotatable shaft 70. A piezoelectric motor 120 has slip ring assemblies 122, 124 incorporated into it. Slip ring assemblies 122, 124 include stationary contacts 130, 132 and rotational contacts 134, 136. Slip ring assemblies 122, 124 facilitate transfer of signals between stationary contacts 130, 132 and rotational contacts 134, 136.

Motor 120 is of a type which uses a piezoelectric element capable of converting between mechanical and electrical energy to provide a driving vibrational motion. A stator 125 is secured to wall 24 such that it doesn't rotate relative to wall 24. The piezoelectric element is incorporated into stator 125. In some designs, the piezoelectric element could be constructed as stator 125. In other designs one or more piezoelectric elements could be attached to stator 125. Clutches are positioned at either axial end of stator 125 and are disposed on shaft 70 such that they rotate with shaft 70 and are rotatable relative to stator 125. A spring 138 ensures that the clutches and stator 125 are always in contact with relatively constant force. In a typical arrangement, an energized piezoelectric element will act upon the clutches and cause the clutches to rotate relative to the stator. In this embodiment, the mechanical connection between the clutches and stator are used to create a slip ring. Accordingly, the clutches also serve as rotational contacts 134, 136. Shaft 70 is constructed from an electrically insulating material or alternatively, an insulative coating can be added between rotational contacts 134, 136 and shaft 70 in order to electrically isolate rotational contact 134 from rotational contact 136. Stationary contacts 130, 132 are positioned in mechanical connection with rotational contacts 134, 136 and are generally disc shaped and extend circumferentially around the rotation axis. The stationary and rotational contacts are created of a material which is suitable for conducting electrical signals which is usually but not necessarily a metal. In some cases, the contacts could be coated with a conductive layer. Insulating layers 126, 128 are positioned between stator 125 and stationary contacts 130, 132. Insulating layers 126, 128 are generally disc shaped and extend circumferentially around the rotation axis. Insulating layers 126, 128 are created of any suitably electrically insulating material (and/or an insulative coating) and provide electrical insulation between stationary contacts 130, 132 and stator 125.

Slip ring assemblies 122, 124 provide a conduction pathway between stationary contacts 130, 132 and rotational contacts 134, 136, which is a part of a conduction pathway between transducer 28 and the ultrasound console. Conductor 117 is connected to rotational contact 136, and conductor 118 is connected to rotational contact 134. Conductor 115 is connected to stationary contact 130, and conductor 116 is connected to stationary contact 132. Conductors 117, 118 are configured to pass through the wall of shaft 70 and couple with rotational contacts 134, 136 using any suitable means which provides insulation between the conductors and the shaft wall, such as for example using insulated wires. Conductors 115, 116 extend throughout the catheter 22 to eventually conductively connect with the ultrasound console. Rotational contacts 134, 136 and stationary contacts 130, 132 each have a surface which is suitable to maintain a mechanical connection between the rotational contacts and stationary contacts even while rotational contacts 134, 136 rotate relative to stationary contacts 130, 132. A suitable metallic coating or lubrication could be used for example.

The design of FIG. 4 is advantageous because it minimizes the extra space and components needed to incorporate a slip ring into device 20. Two slip ring assemblies 122, 124 are included. However, the design could be described as a single slip ring assembly that includes both conduction paths. In the FIG. 4 embodiment, a two channel electrical connection includes conductor 117 as a signal channel and conductor 118 as a ground channel. Conductors 117, 118 can be attached to transducer 28 in a variety of ways as described herein.

Figure 5:
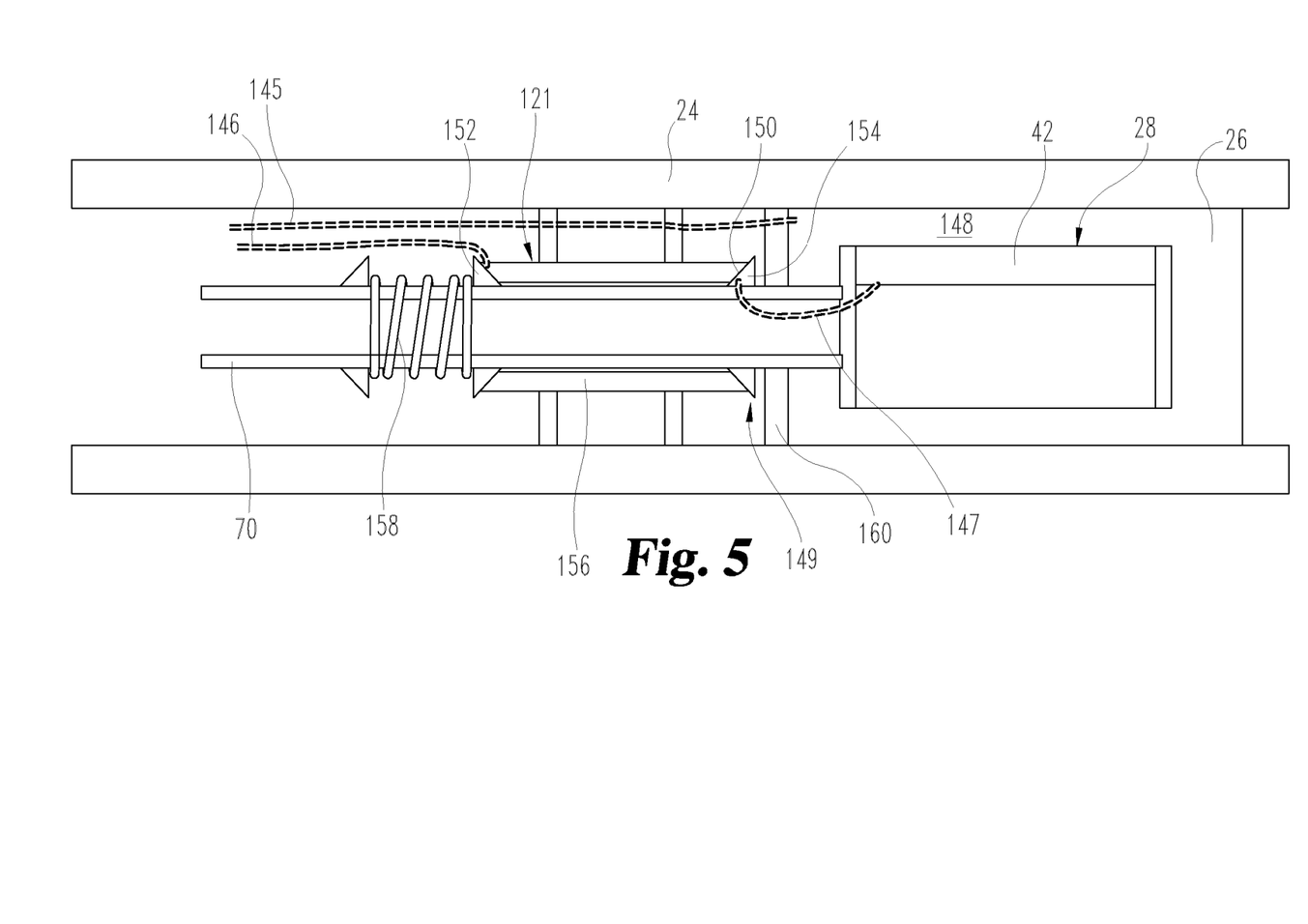
FIG. 5 is a cross-sectional view of an ultrasound imaging device with a slip ring assembly included in a motor, and a fluid acting as a conductor.

A further alternative embodiment of device 20 is shown in FIG. 5. In this embodiment electric signals are passed between the ultrasound console and transducer 28 via conductors 145, 146, 147, 148. A piezoelectric motor 121 has a one channel slip ring assembly 149 incorporated into it. The slip ring assembly 149 includes stationary contact 150 and rotational contact 154. The slip ring assembly 149 facilitates transfer of signals between stationary contact 150 and rotational contact 154.

Motor 121 is a piezoelectric motor as described previously. A stator 156 has at one end a stationary contact 150. Stator 156 is secured to wall 24 such that it doesn't rotate relative to wall 24. The piezoelectric element is incorporated into stator 156 as described previously. Rotational contact 154 serves as a clutch positioned on the application side end of stator 156. An additional clutch 152 is positioned on the contact side end of stator 156. Rotational contact 154 and clutch 152 are disposed on shaft 70 such that they rotate with shaft 70 and are rotatable relative to stator 156. A spring 158 ensures that rotational contact 154 and clutch 152 are always in contact with stator 156 with relatively constant force. An energized piezoelectric element will act upon one or both of rotational contact 154 and clutch 152 and cause rotational contact 154 and clutch 152 to rotate relative to stator 156. The mechanical connection between rotational contact 154 and stator 156 (stationary contact 150) is used to create a slip ring. Rotational contact 154 and stator 156 are created of a material which is suitable for conducting electrical signals which is usually but not necessarily a metal. Additionally, stationary contact 150 and rotational contact 154 each have a surface which is suitable to maintain a mechanical connection between rotational contact 154 and stationary contact 150 even while rotational contact 154 rotates relative to stationary contact 150. In some cases, rotational contact 154 and stator 156 could be coated with a conductive layer or lubrication. A suitable metallic coating could be applied for example, such as cobalt-doped gold, platmium, or rhodium for example.

Conductor 148 is a fluid conductor. A seal 160 or other structure is positioned near motor 121 and shaft 70 to provide a fluid seal between the motor and the chamber 26 surrounding transducer 28. Conductor 145 is conductively coupled with conductors 148 and is disposed to sealingly pass through seal 160. Conductor 148 provides an electric conduction path between an element 42 of transducer 28 and conductor 145. Alternatively, a matching layer could be a conductor which is part of a conduction path between element 42 and conductor 148. Conductor 148 can be any of a variety of electrically conductive fluids as discussed previously. Conductor 110 has acoustic properties similar to wall 24 and body fluids in order to provide matching acoustic characteristics between conductor 148, wall 24, and body fluids, as well as lubricious qualities and other characteristics as described in relation to the embodiment of FIG. 1.

Slip ring assembly 149 provides a one channel conduction pathway between stator 156 and rotational contact 154 which is part of a two channel conduction pathway between transducer 28 and the ultrasound console. The first pathway has a rotatable portion which extends from transducer 28 via conductor 147 through shaft 70 to rotational contact 154. The first pathway then extends through stator 156 and conductor 146. The second pathway extends from transducer 28 through fluid conductor 148 to conductor 145. Conductors 145, 146 extend throughout the catheter 22 to eventually conductively connect with the ultrasound console.

The design of FIG. 5 is advantageous because it minimizes the extra space and components needed to incorporate a slip ring into device 20 as well as reducing complexity of motor 121. In the FIG. 5 embodiment, a two channel electrical connection includes conductor 148 as a signal channel and conductor 147 as a ground channel, or vice versa. Conductor 147 can be attached to transducer 28 in a variety of ways as already described.

The design of FIG. 5 which includes as one channel a conductive fluid surrounding transducer 28 could be incorporated into each embodiment described herein by creating each various slip ring assembly as a one channel conductor and using conductive fluid as a second channel.

Figure 6:
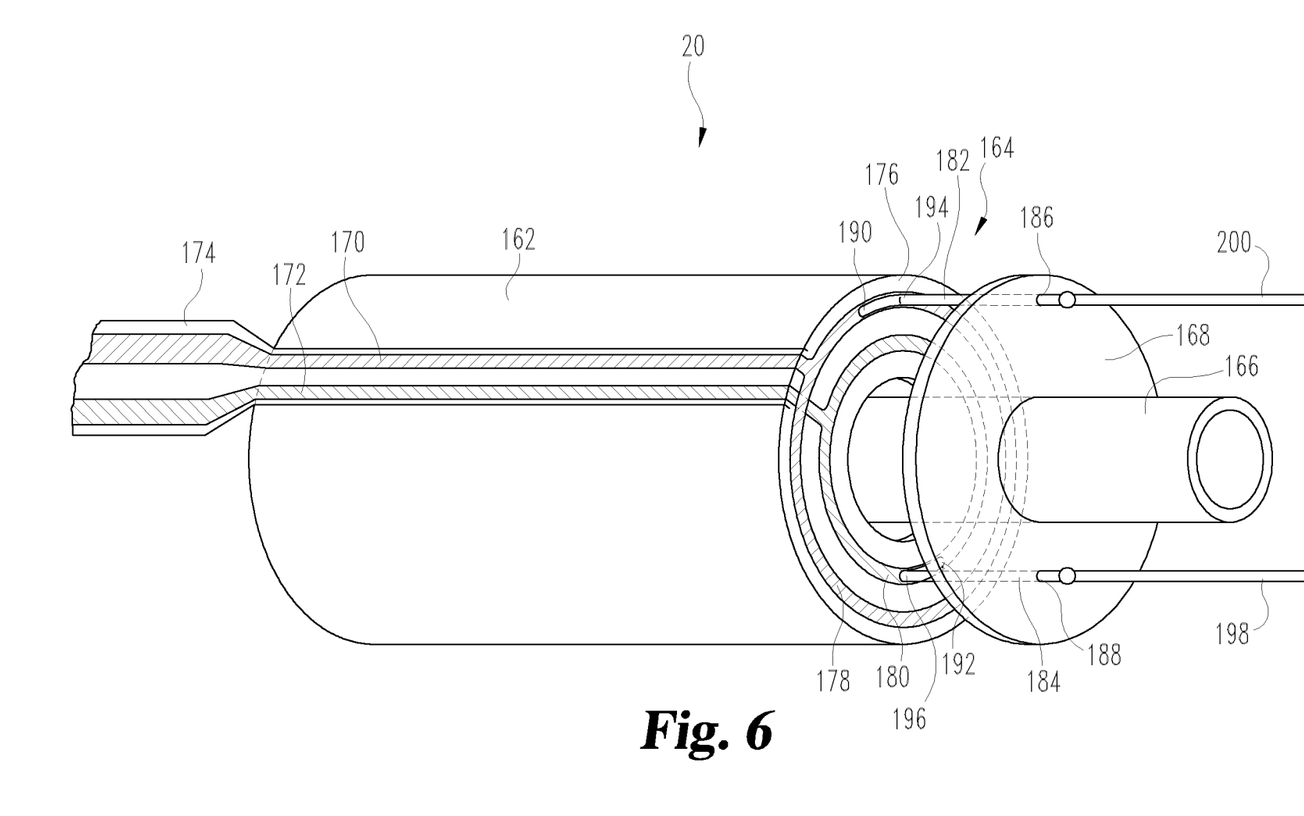
FIG. 6 is a cross-sectional view of an ultrasound imaging device with a slip ring assembly positioned adjacent to an application side end of the motor.

A further alternative embodiment of device 20 is shown in FIG. 6. In the embodiment of FIG. 6, electronic signals pass between an ultrasound console and transducer 28 through both a fixed conduction pathway and a rotatable conduction pathway which are joined by a slip ring assembly 164 which is incorporated with or attached to a motor 162. Slip ring assembly 164 includes rotational contacts 182, 184 and stationary contacts 178, 180. Slip ring assembly 164 and motor 162 are configured to be disposed in device 20 in a similar manner as previously described (e.g. within catheter 22). Slip ring assembly 164 is a type having a rotating surface and a stationary surface positioned parallel to each other and normal to the rotation axis. Each surface carries conductors which interact with conductors on the opposing surface. This is sometimes referred to as a pancake-style slip ring assembly.

Motor 162 is a microminiature motor of a small size as previously described, and could be a piezoelectric motor, electromagnetic motor, or shape memory motor, for example. Motor 162 is operatively coupled with a rotatable shaft 166. Shaft 166 can be solid or a hollow cylindrical shaft having a lumen extending therethrough. Transducer 28 is operatively connected to shaft 166 so that transducer 28 rotates in response to rotation of shaft 166.

Conductors 170, 172 are incorporated with motor 162 through use of a PCB cable or other suitable means. In the FIG. 6 example, a PCB cable 174 runs along a stator or outer portion of motor 162 from a control side of motor 162 to an application side end of motor 162. The PCB cable 174 extends throughout catheter 22 to conductively couple with an ultrasound console. A shoulder 176 is positioned on the application side end of motor 162, and more particularly on the application side end of the stator of motor 162. Shoulder 176 includes stationary contacts 178, 180 which extend circumferentially about the rotation axis in an annular configuration. Stationary contacts 178, 180 are exposed portions of conductive material (e.g. metal) which are configured to mechanically interact with rotational contacts 182, 184. Stationary contact 178 is positioned radially outward from stationary contact 180 with respect to the rotation axis. In other words, stationary contacts 178, 180 are arranged concentrically with respect to the rotation axis. Shoulder 176 can include a separate disk positioned at the application side end of motor 162. Alternatively shoulder 176 can be an integral part of cable 174 wherein the application side end of cable 174 is shaped as a disk shaped shoulder 176. Stationary contact 178 is conductively coupled with conductor 170 and is electrically insulated from stationary contact 180. Conductor 172 is electrically insulated from stationary contact 178 and conductor 170. Stationary contact 180 is conductively coupled with conductor 172.

A disk 168 is coupled with shaft 166 such that it is substantially normal relative to the rotation axis. Disk 168 includes a centrally positioned hole which is sized to fit shaft 166. Alternatively, disk 168 can be an integral part of shaft 166. Disk 168 can be connected to shaft 166 by glue or any other suitable means. Disk 168 rotates along with shaft 166 such that it rotates relative to shoulder 176. Disk 168 is positioned substantially parallel to shoulder 176. Disk 168 includes holes 186, 188 which are configured to accept and anchor rotational contacts 182, 184. Disk 168 can be constructed of any suitably rigid material, such that it substantially maintains its shape while shaft 166 rotates. Disk 168 can be constructed of a suitable nonconductive material such that it does not provide a conduction path between rotation contact 182 and rotation contact 184. Alternatively disk 168 can include an insulative coating.

Rotational contacts 182, 184 extend from disk 168 to mechanically couple with stationary contacts 178, 180. Rotational contact 182 is positioned radially outward from rotational contact 184 relative to the rotation axis. Rotational contact 182 is positioned to mechanically interact with stationary contact 178 and rotational contact 184 is positioned to mechanically interact with stationary contact 180. Rotational contacts 182, 184 can be any suitable contact such as a metal filament or wire. Rotational contacts 182, 184 include ends 190, 192 which are positioned to maintain a mechanical connection with stationary contacts 178, 180 while disk 168 rotates. Rotational contacts 182, 184 extend axially from disk 168 in a control side direction towards shoulder 176 and include bends 194, 196 near the control side of the contacts which facilitate the mechanical connection with stationary contacts 178, 180. Bends 194, 196 can be configured to cause elastic force to apply pressure between ends 190, 192 and stationary contacts 178, 180. In this way, rotational contacts 182, 184 form a slipping electrical contact with stationary contacts 178, 180 which allow rotational contacts 182, 184 to maintain a conductive coupling with stationary contacts 180, 182 while transducer 28 rotates. Conductor 198 is coupled with the application side of rotational contact 184 and conductor 200 is coupled with the application side of rotational contact 182. Conductors 198, 200 can be coupled with rotational contacts 182, 184 using any suitable means such as soldering for example.

Slip ring assembly 164 provides a two channel conduction pathway between rotational contacts 182, 184 and stationary contacts 178, 180 which is part of a conduction pathway between transducer 28 and the ultrasound console. Conductors 198, 200 can extend through an optional hole in the wall of shaft 166 and continue through a shaft lumen to couple with transducer 28. Conductors 170, 172 extend throughout the catheter 22 to eventually conductively connect with the ultrasound console. PCB cable 174 may or may not extend throughout the length of catheter 22. Rotational contacts 182, 184 and stationary contacts 180, 182 each have connection surfaces which are suitable to maintain a mechanical connection between rotational contacts and stationary contacts even while rotational contacts 182, 184 rotate relative to stationary contacts 178, 180. A suitable metallic coating or lubrication could be used for example.

The design of FIG. 6 is advantageous because it minimizes the extra space and components needed to incorporate a standalone slip ring into device 20. Slip ring assembly 164 is described with a two channel connection. However the slip ring design could incorporate a single channel connection in which a second channel could include a conductive fluid surrounding transducer 28 and a conductor extending from the fluid through the catheter to the control side of motor 162 (as described herein).

In an alternative embodiment (not shown), slip ring assembly 164 could include axially-protruding contacts 182, 184 being positioned on shoulder 176 and conductively coupled with conductors 170, 172. In that case, contacts 182, 184 are stationary relative to the rotation axis and are configured to interact with annular and concentrically-arranged rotational contacts positioned on disk 168 and which are conductively coupled with conductors 198, 200. In this embodiment, ends 190, 192 form a sliding contact with the rotational contacts positioned on the disk 168 as disk 168 rotates about the rotation axis.

The embodiments described herein, including use of slip ring assemblies, allows device 20 to include a directly rotating transducer element which avoids the need for use of a rotating mirror design and the disadvantages associated with such design. For example, device 20 is shorter and takes up less space than a rotating mirror design. The directly rotating transducer embodiments described herein have a deeper acoustic focal depth than a rotating mirror design. In the disclosed embodiment, ultrasound waves are generated in a generally radial direction with respect to the rotation axis (i.e. the catheter axis) as opposed to a reflector design in which ultrasound waves must travel axially (relative to the rotation axis) for several millimeters before beginning to travel in a radial direction.

The slip ring embodiments described herein are not limited to the uses described herein. For example, the slip ring assemblies can be incorporated in any ultrasound device which incorporates a rotating element. Some examples could include a linear motor with a rotary drive shaft, a linear motor which connects to mechanical connections to convert linear movement to rotary movement, or a gearing assembly positioned between a drive shaft and a transducer.

As an additional advantage, device 20 facilitates capture of an image through a viewing window which is free from unnecessary artifacts, obstructions, or errors within the image. For example, positioning of transducer 28 at a location which is on an application side of motor 32, conductors 50, 52, and other components ensures that wires or other echogenic materials are not positioned within or across the viewing window of transducer 28, even as transducer 28 rotates in a full 360° rotation. In this way, there are no wires or other echogenic materials which could cause artifacts within the image or block portions of the redirected ultrasound waves, which provides the physician a clear view of the entirety of the viewing window. As used herein, the term "window" includes an obstruction-free pathway extending throughout the structure of device 20 and optional surrounding bodily fluid and/or tissue between transducer 28 and tissue which is to be imaged.

As an additional advantage, motor 32 which is separate from and positioned near the application end of a catheter allows a uniform angular velocity to be achieved by transducer 28. This uniform angular velocity results in an ultrasound image which is free from non-uniform rotational defects (NURD) which can otherwise be a problem with the designs using torque cables and relatively remote motors or rotational power sources.

Device 20 is configured to be used with existing medical devices which are designed for percutaneous, intraluminal, or interstitial procedures. For example, device 20 can be used with a variety of commercially available catheters, e.g. positioned on or within an application side of a catheter depending on the particular configuration. Device 20 can be positioned within an existing lumen within the catheter. In an alternative embodiment, device 20 could include an external casing which is similar to catheter 22 having walls 24 but being shortened so as to compactly contain device 20. Device 20 could be mounted externally to a catheter using a variety of mounting devices, glues or other types of arrangements. It will be understood by those skilled in the art that the particular type of mounting procedure for the device 20 to an existing medical device can include a variety of different types of mounting methods. Accordingly, the particular methods described herein are not indicative of any limiting aspects of the usage capabilities of the device 20.

Other features may be included with the embodiments noted herein such as indexing systems, three-dimensional ultrasound devices, and gearing assemblies. Either one or both of the rotational contacts and stationary contacts disclosed herein can include a biasing member disposed to maintain sufficient force between the stationary contacts and rotational contacts. The contacts in all cases can include a coating including precious metals or other suitable material which prevents or minimized oxidation. In each embodiment, the slip ring assemblies can include an encapsulating structure which can be filled with a fluid to reduce friction between the rotational contacts and stationary contacts and/ or prevent oxidation.

While device 20 is described in part above in the context of ultrasound system applications, it will be understood that embodiments of device 20 could also be used for other medical procedures and/or with a variety of other medical devices. The versatility of the embodiments described herein allows device 20 to be used to guide percutaneous therapeutic interventions such as for example embolism coils, stents, filters, graphs, balloons, biopsies, and ministering therapeutics, etc. Device 20 can be used to locate various anatomical landmarks that will be used to correctly place or guide therapy. Typical landmarks include confluences, bifurcations, side branches, nearby vessels, nearby nerves, the heart, and other tissues adjacent to vessels or other orifices containing the IVUS transducer. Device 20 can also be used to locate diseased tissue that will be treated or avoided. Device 20 can be used during a biopsy to provide an image of a needle being deployed into tissue. During a TIPS procedure an image can be produced to allow a physician to watch a needle being placed into the portal vein. For AAA delivery, device 20 can allow a physician to place a guide wire into a contralateral leg. Device 20 could also be used to image the location of a deployed implantable device both during and after deployment.

Although particular materials were highlighted herein for some components of the device 20, those materials are not intended to be limiting of the types of materials which are suitable to be used in the device 20. Additionally, where materials have were not highlighted, a variety of materials could be used such as certain types of metals, polymers, ceramics or other types of materials which are suitable for use in devices for subcutaneous use as well as IVUS imaging procedures.

The device 20 could also be used for a variety of other medical procedures and with a variety of other medical devices. It will be understood by those skilled in the art that the particular type of mounting procedure can include a variety of different types of mounting methods. Accordingly, the particular methods described herein are not indicative of any limiting aspects of the usage capabilities of the device 20.

While the invention has been illustrated and described in detail in the drawings and foregoing description, the same is to be considered as illustrative and not restrictive in character, it being understood that only the preferred embodiments have been shown and described and that all changes, equivalents, and modifications that come within the spirit of the inventions defined by the following claims are desired to be protected. It will be understood that structures or other features described with respect to one particular embodiment or item may be used in connection or along with other features, items or embodiments included herein. Alternative embodiments of device 20 include various configurations of slip ring assemblies disclosed herein. The structural and operational details disclosed herein are intended to apply to each embodiment with the exception of the specific differences described herein between the various embodiments.

What is claimed is:

1. A medical ultrasound device, comprising:
a motor operatively coupled with a drive shaft extending substantially along a rotation axis, wherein operation of the motor rotates the drive shaft around the rotation axis;
a transducer configured for transmitting and/or receiving ultrasound signals and operatively coupled with the drive shaft so that the transducer rotates in response to rotation of the drive shaft;
a first slip ring assembly having a first rotational contact and a first stationary contact, the first rotational contact being fixed to the drive shaft and rotatable with the drive shaft relative to and in contact with the first stationary contact, wherein the first slip ring assembly maintains an electrical conduction path between the first rotational contact and the first stationary contact when the drive shaft rotates;

a second slip ring assembly having a second rotational contact and a second stationary contact, the second rotational contact being fixed to the drive shaft and rotatable with the drive shaft relative to and in contact with the second stationary contact, wherein the second slip ring assembly maintains an electrical conduction path between the second rotational contact and the second stationary contact when the drive shaft rotates; and wherein the first and second rotational contacts are electrically conductive layers fixed with respect to the drive shaft, further comprising an insulating layer wherein the first rotational contact is positioned radially inward of the second rotational contact, and the first and second rotational contacts are separated by the insulating layer, wherein the first rotational contact and the insulating layer have respective lengths measured parallel to a rotation axis of the drive shaft, and wherein the length of the first rotational contact is larger than the length of the insulating layer, wherein at least one axially outer portion of the first rotational contact is exposed from the insulating layer, wherein the second rotational contact has a length measured parallel to a rotation axis of the drive shaft, and wherein the length of the insulating layer is larger than the length of the second rotational contact.

2. The device of claim 1, wherein two axially outer portions of the insulating layer are exposed from the second rotational contact.

3. The device of claim 1, wherein the first stationary contact is integrally attached to the motor.

4. The device of claim 1, wherein the medical ultrasound device includes an application side and a control side, and wherein the first rotational contact and first stationary contact are in contact with each other at a point on the application side of the insulating layer, and the second rotational contact and second stationary contact are in contact with each other at a point on the control side of the insulating layer.

5. The device of claim 1, further comprising an insulating section disposed between the first stationary contact and the second stationary contact, and disposed to contact the insulating layer.

6. The device of claim 1, wherein the first and second rotational contacts are part of a three layer coating, the first rotational contact being a radially inward first layer, the insulating layer being a second layer, and the second rotational contact being a radially outward third layer, wherein the insulating layer partially covers the first rotational contact and the second rotational contact partially covers the insulating layer.

7. The device of claim 1, further comprising a fluidly sealed chamber enclosing the transducer and having an interior in fluid communication with the first stationary contact and the transducer, wherein the chamber is configured to receive a fluid, whereby when an electrically conductive fluid is disposed within the chamber, the electrically conductive fluid creates a conduction path between the transducer and either the first stationary contact or the second stationary contact.

8. The device of claim 1, further comprising a biasing member disposed to apply a force which maintains contact between the first rotational contact and the first stationary contact.

9. The device of claim 1, further comprising an encapsulating structure fillable and positioned to enclose at least one slip ring assembly with a fluid whereby the fluid reduces friction and/or prevents oxidation.

10. A medical ultrasound device, comprising:

a transducer configured for transmitting and/or receiving ultrasound signals and operatively coupled with a drive shaft extending substantially along a rotation axis, wherein the transducer rotates in response to rotation of the drive shaft; and a motor operatively coupled with the drive shaft, wherein the motor includes a first slip ring assembly having a first rotational contact and a first stationary contact, the first rotational contact being fixed relative to the drive shaft and rotatable with the drive shaft relative to and in contact with the first stationary contact, the motor further comprising a stator, wherein the first stationary contact is incorporated into the motor and fixed relative to the stator, wherein the first slip ring assembly maintains an electrical conduction path between the first rotational contact and the first stationary contact when the drive shaft rotates;

wherein the motor further comprises a second slip ring assembly having a second rotational contact and a second stationary contact, the second rotational contact being fixed relative to the drive shaft and rotatable with the drive shaft relative to and in contact with the second stationary contact, wherein the second slip ring assembly maintains an electrical conduction path between the second rotational contact and the second stationary contact when the drive shaft rotates, wherein the first rotational contact is electrically insulated from the second rotational contact and the first stationary contact is electrically insulated from the second stationary contact; and, wherein the motor is a piezoelectric motor including a stator and a first clutch coupled with the shaft and disposed to engage a piezoelectric element, wherein the first clutch includes the first rotational contact, the motor further comprising a second clutch coupled with the shaft, wherein the second clutch includes the second rotational contact, wherein the stator includes a first end and a second end, wherein the second end is positioned opposite the first end in an axial direction relative to the rotation axis, wherein the first clutch is disposed adjacent to the first end and the second clutch is disposed adjacent to the second end.

11. The device of claim 10, wherein the stator includes the first stationary contact.

12. The device of claim 10, further comprising a first insulating layer positioned between the first stationary contact and the first end, and a second insulating layer positioned between the second stationary contact and the second end.

13. The device of claim 10, further comprising a first end of the first rotational contact disposed to contact the first stationary contact and a second end of the second rotational contact disposed to contact the second stationary contact, wherein during rotation of the drive shaft, the first end follows a first circumferential path about the rotation axis and the second end follows a second circumferential path about the rotation axis, wherein the first circumferential path is positioned concentric to and radially inward of the second circumferential path, and wherein the first stationary contact is positioned radially inward of the second stationary contact.

14. The device of claim 10, further comprising a first end of the first stationary contact disposed to contact the first rotational contact and a second end of the second stationary contact disposed to contact the second rotational contact, wherein the second end is positioned radially outward from the first end relative to the rotation axis, and wherein the second rotational contact is positioned concentric to and radially outward of the first rotational contact.

15. The device of claim 13, further comprising a disk coupled with the shaft and anchoring the first and second rotational contacts.

16. The device of claim 10, further comprising a conductor and a fluidly sealed chamber enclosing the transducer and having an interior in fluid communication with the conductor and the transducer, wherein the chamber is configured to receive a fluid, whereby when an electrically conductive fluid is disposed within the chamber, the electrically conductive fluid creates a conduction path between the transducer and the conductor.

17. The device of claim 10, further comprising a biasing member disposed to apply a force which maintains contact between the first rotational contact and the first stationary contact.

18. The device of claim 10, wherein at least one of the contacts is coated with a precious metal.

* * * * *